United States Patent [19]

Ogunbiyi et al.

[11] Patent Number: 4,786,436
[45] Date of Patent: Nov. 22, 1988

[54] WETTING SOLUTIONS FOR CONTACT LENSES

[75] Inventors: Lai Ogunbiyi, Fairport; Francis X. Smith, Walworth, both of N.Y.

[73] Assignee: Bausch & Lomb Incorporated, Rochester, N.Y.

[21] Appl. No.: 106,961

[22] Filed: Oct. 14, 1987

Related U.S. Application Data

[63] Continuation of Ser. No. 824,484, Jan. 31, 1986, abandoned.

[51] Int. Cl.$^4$ .......................... B01F 17/00; B01F 17/30
[52] U.S. Cl. ................................... 252/352; 252/106; 252/356; 514/774; 514/801; 514/839
[58] Field of Search ................. 106/124, 125; 252/106, 252/173, 174.23, 356, DIG. 14; 514/774, 801, 839, 840; 530/354, 356

[56] References Cited

FOREIGN PATENT DOCUMENTS 2616939 10/1977 Fed. Rep. of Germany .

OTHER PUBLICATIONS

Kahn, Leo, D., Biochima et Biophysica Acta", Some Effects of Electrolytes on Collagen in Solution", 63(1962), 243-254.

Primary Examiner—Prince E. Willis
Attorney, Agent, or Firm—Christopher E. Blank; Craig E. Larson; Bernard D. Bogdon

[57] ABSTRACT

An improved wetting solution for contact lenses is disclosed. The solution contains collagen as a wetting agent and preferably a biguanide as a preservative.

6 Claims, 1 Drawing Sheet

WETTING SOLUTIONS FOR CONTACT LENSES

This is a continuation of copending application Ser. No. 824,484 filed on Jan. 31, 1986 now abandoned.

BACKGROUND OF THE INVENTION

1. Field of the Invention

This invention relates to improved wetting solutions for contact lenses and contact lens care solutions.

2. Description of the Prior Art

Contact lenses in wide use today fall into two categories. First, there are the hard or rigid corneal type lenses that are formed from materials prepared by the polymerization of acrylic esters, such as polymethyl methacrylate (PMMA). Secondly, there are the gel, hydrogel or soft type of lenses made by polymerizing such monomers as 2-hydroxyethyl methacrylate (HEMA).

Cleaning, storing and wetting solutions are required for both the hard and the soft types of contact lenses. These solutions usually contain a wetting agent to enhance wearer comfort in combination with a germicide or preservative, a viscosity builder and salts that adjust the tonicity of the solutions to make them compatible with the osmolality of the tear fluids. U.S. Pat. No. 4,323,467 describes wetting solutions that may contain gelatin as a viscosity builder and the gelatin is used in an amount sufficient to achieve a viscosity of the solution of 15–750 CPS at 25° C.

The hard acrylic type of contact lenses are highly durable and, since they do not absorb appreciable amounts of water, the selection of suitable disinfecting agents, cleaning agents or other lens care compounds is relatively non-critical.

However, unlike hard lenses, the soft type of contact lens and certain of the newer gas permeable hard contact lenses have a tendency to bind and concentrate significantly more fluids, environmental pollutants, water impurities, as well as antimicrobial agents found in lens care solutions. In most instances, the low levels of the ingredients in lens care solutions do not lead to eye tissue irritation when used properly. Nevertheless, because of the inherent binding action of protein deposits and soft lens materials, disinfecting agents and preservatives tend to build up on lens surfaces and become concentrated to potentially hazardous levels, such that corneal inflammation and other eye tissue irritation can result.

Previous efforts to alleviate the problem of binding and concentrating disinfectants and preservatives onto contact lens surfaces and reducing the potential for eye tissue irritation have not been totally satisfactory. For example, in spite of low toxicity levels, not all disinfectants are compatible for use with all types of contact lenses. Many hard lens disinfecting and preservative solutions contain benzalkonium chloride or chlorobutanol. Although they are effective antibacterial agents, their use can result in a loss of lens hydrophilic properties, cause solution instability or may even lack compatibility with certain types of hard lenses, e.g., high silicon content.

Other antibacterial agents were found to be more compatible with contact lenses and exhibit less binding on lens surfaces. Such agents are disclosed in U.S. Pat. Nos. 4,354,952, 4,361,548 and British Pat. No. 1,432,345. However, these compositions have exhibited serious disadvantages, and there is a need for improved disinfecting and preservative solutions which are compatible for use with most types of contact lenses while maintaining both a high level of antibacterial activity and low order of toxicity to eye tissue with little or no binding or concentrating of the disinfecting agent onto lens surfaces.

We have found that collagen can be used in contact lens care solutions in amounts such that the viscosity of the solution is substantially lower than the viscosity of prior art contact lens care solutions and that the collagen in our solutions is a highly effective wetting agent or demulcent. We have also found that the collagen-containing solutions of our invention can also contain microbicidally effective amounts of certain biguanides or water-soluble salts thereof in such relatively small amounts that many of the problems of the prior art preservative and disinfectants are overcome.

SUMMARY OF THE INVENTION

In accordance with this invention, there is provided a contact lens wetting solution that contains collagen in an amount such that the viscosity of the solution is substantially less than 15 CPS at 25° C. There is also provided a contact lens solution having a viscosity substantially less than 15 CPS at 25° that contains collagen and a microbicidally effective amount of a biguanide or water soluble salt thereof.

DESCRIPTION OF THE PREFERRED EMBODIMENTS

Figure 1:
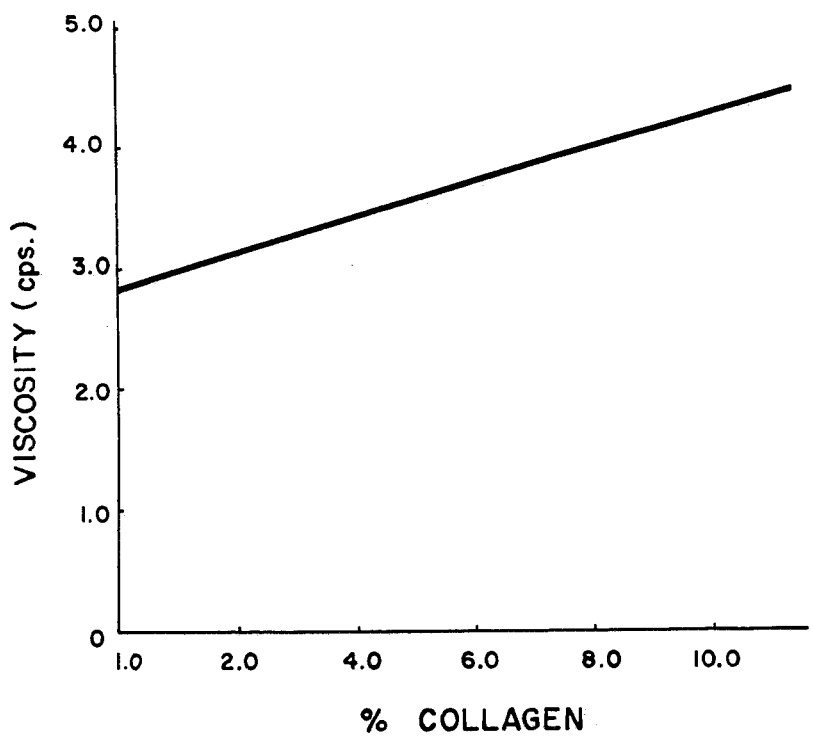

The solutions of this invention contain collagen in an amount so that the viscosity of the solution is substantially less than 15 CPS at 25° C. The amount of collagen that is used is less than 10% by weight of the solution and preferably not more than 1% by weight. Most preferably, the amount of collagen is within the range of 0.001% to 1.0% by weight.

Collagen can be obtained from calfskin, steer hide, cowhide, pigskin or other starting material. After dehairing and cleaning, the skin can be solubilized with an enzyme. The enzyme is inactivated with a caustic. Subsequently the solubilized collagen is defatted to obtain a clear collagen gel.

The chemistry, chemical properties and molecular structure of collagen are well known and collagen has been used in a number of drug and medical applications.

In addition to collagen, the solutions of this invention may also contain other water soluble demulcents. Other demulcents are not required but among the demulcents that may be present are gelatin and the water soluble cellulose derivatives, such as hydroxyethyl cellulose, methyl cellulose, carboxymethyl cellulose, hydroxypropyl methylcellulose, hydroxypropyl cellulose and the like. When other demulcents are used in addition to collagen, the viscosity of the solution will be less than 15 CPS at 25° C.

The solutions of this invention will also contain water and one or more other components which are commonly present in contact lens care solutions, such as surfactants, germicides, buffering agents, tonicity agents and sequestering aqents.

Any surfactant that is known to be useful in contact lens wetting solutions can be used in the solutions of this invention. A preferred nonionic surfactant is a poly(oxypropylene)-poly(oxyethylene) adduct of ethylenediamine having a molecular weight of 7,500 to 27,000 wherein at least 40 percent of the adduct is poly(oxyethylene). The adduct is used in an amount within the range of 0.01 to 15 percent by weight of the solution.

This surfactant, which can be called a poloxamine, is marketed under the trademark "Tetronic".

Any of the known buffering agents for contact lens wetting solutions can also be used. For example, any of the phosphate buffers can be used, but the borate buffers, such as boric acid, sodium borate, potassium tetraborate, potassium metaborate or mixtures thereof are preferred Other buffers are sodium or potassium citrate, citric acid, sodium bicarbonate and various mixed phosphate buffers such as $Na_2HPO_4$, $NaH_2PO_4$ and $KH_2PO_4$. The buffers are used in an amount within the range of 0.05 to 2.5 percent by weight, preferably from 0.1 to 1.5 percent by weight.

The aqueous solutions for treating contact lenses preferably contain tonicity agents so that the osmotic pressure of the solution approximates normal lacrimal fluids which is equivalent to an 0.9 percent by weight solution of sodium chloride or a 2.5 percent by weight of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

The solutions also preferably contain a sequestering agent. Many organic acids, amines or compounds which include an acid group and an amine function are capable of acting as sequestering compounds. For example, diethylenetriamine-pentacetic acid, 1,2 diaminocyclohexane tetracetic acid, hydroxyethylaminodiacetic acid, ethylenediaminetetracetic acid and its salts, polyphosphates, citric acid and its salts, tartaric acid, and the like are useful sequestering agents. Ethylenediaminetetracetic acid and its alkali metal salts are preferred. The most preferred agent is the disodium salt of ethylenediamine-tetracetic acid, also known as disodium edetate.

The solutions also preferably contain a microbicidally effective amount of a germicide or disinfectant. Suitable germicides include thimerosal, sorbic acid, 1,5 pentanedial, alkyl triethanolamines, phenylmercuric salts, e.g. nitrate, borate, acetate, chloride and mixtures thereof. The preferred germicide is a biguanide or water soluble salt thereof having the formula

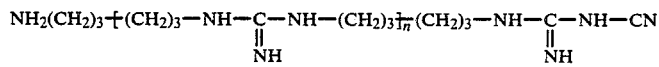

wherein n is from 1 to 500.

The biguanides that are used include hexamethylene biguanides, their polymers and water-soluble salts of such base compounds and polymers. The polymers have molecular weights up to 100,000 and are present in amounts from 0.000001 to 0.0003 weight percent. The solutions may also contain any of the other germicidal agents that are not incompatible with the biguanides.

The biguanide-containing solutions are effective at low concentrations against a wide spectrum of microorganisms including S. epidermidis, C. albicans, A. fumicatus, etc.

The biguanides are much more effective against the various organisms than other disinfectants such as sorbic acid particularly when used at low concentrations. The biguanides can be low molecular weight oligomers where n in the above formula averages from 4 to 7, high molecular weight long chain polymers up to 100,000 M.W., as well as individual monomers of such polymers where is 1. The biguanides also include the water-soluble salts of the free bases, such as hydrochloride and borate salts, acetate, gluconate, sulfonate, tartrate and citrate salts. Preferably, the water-soluble salts are compounds where n has a value of 2 to 12, most preferably 3 to 8. One preferred group of water-soluble biguanides have an average molecular weight of at least 1,000 and more particularly from 1,000 to 50,000.

It is surprising that the lower molecular weight biguanides demonstrate less binding and lower toxicity levels than other disinfectants. Also, monomers, such as hexamethylene biguanide hydrochloride, provide good bactericidal activity at low concentrations with little binding effect as does polyhexamethylene biguanide hydrochloride wherein n is 4 to 7.

U.S. Pat. No. 3,428,576 describes the preparation of biguanides from a diamine and salts thereof and a diamine salt of dicyanimide. This patent teaches methods for making the hydrochloride salt of polyhexamethylene biguanide which is commercially available from ICI Americas, Inc. under the trademark Cosmocil CQ. This biguanide is referred to hereinafter as "PHMB".

The solutions of this invention can be prepared by a variety of techniques. One method includes the preparation of a collagen-containing solution by initially heating about 80 percent of the distilled water to be used to 80° C. With agitation the alkali metal chlorides, sequestering agents, buffering agents, surfactants, and collagen are added in that order. Other demulcents such as hydroxypropylmethyl cellulose and hydroxyethyl cellulose can then be added, if they are to be used. After the solution is cooled to room temperature, the PHMB is added, followed by the balance of distilled water. The solution can then be sterilized by forcing through an 0.22 micron cellulose acetate filter by means of a peristaltic pump and packaged in sterilized plastic containers.

The preservative efficacy of the solutions can be tested by exposing S. epidermis ($1 \times 10^6$ microorganisms/ml), P. aeruginosa ($1 \times 10^6$ microorganisms/ml) and E. Coli ($1 \times 10^6$ microorganisms/ml) each to 20 ml of the solution at room temperature for 14 days. Subsequently, an aliquot sample of each is placed on an agar plate and incubated for 48 hours at elevated temperatures. At the conclusion of the incubation period, the plates are examined for the development of colonies.

The following examples illustrate the invention described above.

EXAMPLE I

In this example collagen-containing contact lens solutions were prepared according to the procedure described above. The solutions contained either PHMB or sorbic acid as a disinfectant/preservative, and the solutions were evaluated by the above test method for effectiveness against S. aureus, P. aerucinosa and E. coli organisms after 14 days. To be considered effective in this test, there must be at least 3 log ($10^3$) reduction in the number of organisms for each type of organism at 14 days. The solutions and test results are shown in the following table.

TABLE I

| Solution | HPMC % | HEC % | Collagen % | Tetronic 1107 % | Boric Acid % | Sodium Borate % | Sodium EDTA % | NaCl % | KCl % | PHMB ppm | Sorbic Acid % |
|---|---|---|---|---|---|---|---|---|---|---|---|
| 1 | 0.20 | 0.40 | 0.20 | 0.0001 | 0.85 | 0.11 | 0.022 | 0.20 | 0.30 | 1.10 | |
| 2 | 0.10 | | 0.10 | 0.50 | 0.85 | 0.12 | 0.022 | 0.20 | 0.30 | 1.10 | |
| 3 | 0.20 | 0.40 | 0.20 | 0.0001 | 0.85 | 0.11 | 0.022 | 0.20 | 0.30 | | 0.11 |
| 4 | 0.10 | | 0.10 | 0.50 | 0.85 | 0.12 | 0.022 | 0.20 | 0.30 | | 0.11 |

TABLE II

| | LOG REDUCTION | | |
|---|---|---|---|
| Solution | S. aureus 14 Days | P. aeriginosa 14 Days | E. coli 14 Days |
| 1 | 6.6 | 6.2 | 6.0 |
| 2 | 6.6 | 6.2 | 6.0 |
| 3 | 6.6 | 6.2 | 1.1 |
| 4 | 6.6 | 6.2 | 1.2 |

In order that the collagen-containing solutions of this invention will function effectively, the viscosity of the solution is preferably below 15 CPS at 25° C. Solutions of various concentrations of collagen in distilled water were prepared. The viscosity of the solution was measured with a Brookfield Viscometer, Model LVT. The observed data are contained in the following table. The viscosity for each collagen concentration is the average of three readings.

| Collagen Concentration | Viscosity (CPS) | |
|---|---|---|
| | Average | Standard Deviation |
| 1.0% | 3.06 | 0.51 |
| 2.0% | 3.00 | 0.20 |
| 3.0% | 3.47 | 0.55 |
| 5.0% | 3.23 | 0.65 |
| 7.0% | 4.40 | 1.96 |
| 10.0% | 4.16 | 0.28 |

These data were used in the preparation of the accompanying curve shown as FIG. 1 to demonstrate the relationship between collagen concentration and solution viscosity.

We claim:

1. An aqueous contact lens wetting solution containing collagen in an amount within the range of 0.001% to 1% by weight, at least one other demulcent in addition to collagen, a buffering agent in an amount within the range of 0.05 to 2.5% by weight and a tonicity agent so that the osmotic pressure of the solution approximates normal lacrimal fluids, the viscosity of the solution being less than 15 CPS at 25° C.

2. An aqueous contact lens wetting solution containing collagen in an amount within the range of 0.001% to 1% by weight, at least one other demulcent in addition to collagen, a buffering agent in an amount within the range of 0.05 to 2.5% by weight, a tonicity agent so that the osmotic pressure of the solution approximates normal lacrimal fluids, and a microbicidally effective amount of a germicide, the viscosity of the solution being less than 15 CPS at 25° C.

3. An aqueous contact lens wetting solution containing collagen in an amount with the range of 0.001% to 1% by weight, at least one other demulcent in addition to collagen, a buffering agent in an amount within the range of 0.05 to 2.5% by weight, a tonicity agent so that the osmotic pressure of the solution approximates normal lacrimal fluids, a microbicidally effective amount of a germicide, and an effective amount of a sequestering agent, the viscosity of the solution being less than 15 CPS at 25° C.

4. An aqueous contact lens wetting solution containing collagen in an amount within the range of 0.001% to 1% by weight, and boric acid and sodium borate as buffering agents, the amount of buffering agent being within the range of 0.05 to 2.5% by weight, the viscosity of the solution being less than 15 CPS at 25° C.

5. An aqueous contact lens wetting solution containing collagen in an amount within the range of 0.001% to 1% by weight, boric acid and sodium borate as buffering agents, the amount of buffering agent being within the range of 0.05 to 2.5% by weight, sodium chloride and potassium chloride as tonicity agents so that the osmotic pressure of the solution approximates normal lacrimal fluids, and a microbicidally effective amount of a biguanide as a germicide, the viscosity of the solution being less than 15 CPS at 25° C.

6. An aqueous contact lens wetting solution containing collagen in an amount within the range of 0.001% to 1% by weight, boric acid and sodium borate as buffering agents, the amount of buffering agent being within the range of 0.05 to 2.5% by weight, sodium chloride and potassium chloride as tonicity agents so that the osmotic pressure of the solution approximates normal lacrimal fluids, and a microbicidally effective amount of the hydrochloride salt of polyhexamethylene-biguanide as a germicide, and an effective amount of disodium edetate as a sequestering agent, the viscosity of the solution being less than 15 CPS at 25° C.

* * * * *